(12) United States Patent
Erdos et al.

(10) Patent No.: US 6,726,983 B2
(45) Date of Patent: Apr. 27, 2004

(54) THERMOCALENDERED NON-WOVEN ELASTIC LAMINATE

(75) Inventors: Valeria Griep Erdos, Huntersville, NC (US); Ellen Mosley, Ventnor, NJ (US)

(73) Assignee: Polymer Group, North Charleston, SC (US)

( * ) Notice: Subject to any disclaimer, the term of this patent is extended or adjusted under 35 U.S.C. 154(b) by 307 days.

(21) Appl. No.: 09/947,976

(22) Filed: Sep. 6, 2001

(65) Prior Publication Data

US 2002/0056510 A1 May 16, 2002

Related U.S. Application Data

(63) Continuation-in-part of application No. 09/370,344, filed on Aug. 6, 1999, now abandoned.

(51) Int. Cl.[7] .......................... B32B 23/02; B32B 27/14; B32B 5/26; D04H 1/00
(52) U.S. Cl. .................... 428/195.1; 428/198; 442/328; 442/381; 442/394; 442/396; 442/409
(58) Field of Search .............................. 428/195.1, 198; 442/328, 381, 394, 396, 409

(56) References Cited

U.S. PATENT DOCUMENTS

| | | |
|---|---|---|
| 4,573,986 A | 3/1986 | Minetola et al. |
| 4,720,415 A | 1/1988 | Vander Wielen et al. |
| 4,842,596 A | 6/1989 | Kielpikowski et al. |
| 4,845,779 A | 7/1989 | Wheeler et al. |
| 4,876,746 A | 10/1989 | Howie |
| 4,981,747 A | 1/1991 | Morman |
| 5,114,781 A | 5/1992 | Morman |
| 5,226,992 A | 7/1993 | Morman |
| 5,336,545 A | 8/1994 | Morman |
| 5,514,470 A | 5/1996 | Haffner et al. |
| 5,655,374 A | 8/1997 | Santilli et al. |
| 5,804,286 A | 9/1998 | Quantrille et al. |
| 5,843,056 A | 12/1998 | Good et al. |
| 6,029,274 A | 2/2000 | Welchel et al. |
| 6,103,647 A | 8/2000 | Shultz et al. |
| 6,198,018 B1 | 3/2001 | Curro |

Primary Examiner—Arti R. Singh
Assistant Examiner—Christopher C Pratt
(74) Attorney, Agent, or Firm—Wood, Phillips, Katz, Clark & Mortimer

(57) ABSTRACT

An elastic laminate fabric useful for applications including apparel, sanitary products, and the like has an elastic vinylidene isoprene polymer film sandwiched between two outer non-woven layers. The laminate elastic fabric has CD elongation of at least 120%, and has recovery of at least 85% after several cycles of 100% elongation. A method of making the non-woven elastic laminate fabric includes extrusion coating a non-woven web having CD elongation of at least 120% with a vinylidene isoprene polymer film, and then thermocalendaring a second non-woven layer having a CD elongation of at least 120% to the exposed film surface. The mode of thermocalendering includes the use of an engraved calender roll having a discontinuous roll pattern and a land area no greater than 15%.

14 Claims, 2 Drawing Sheets

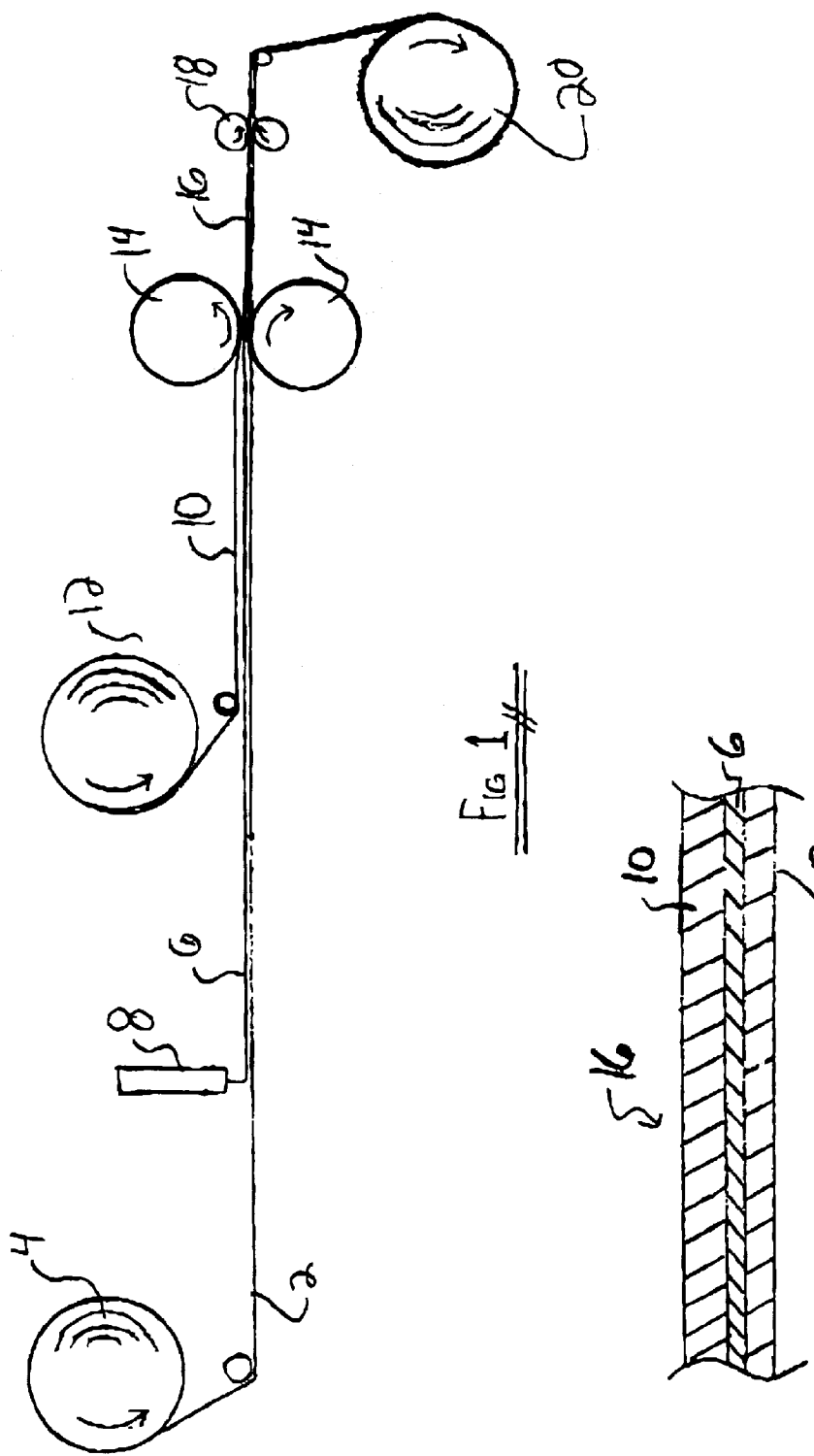

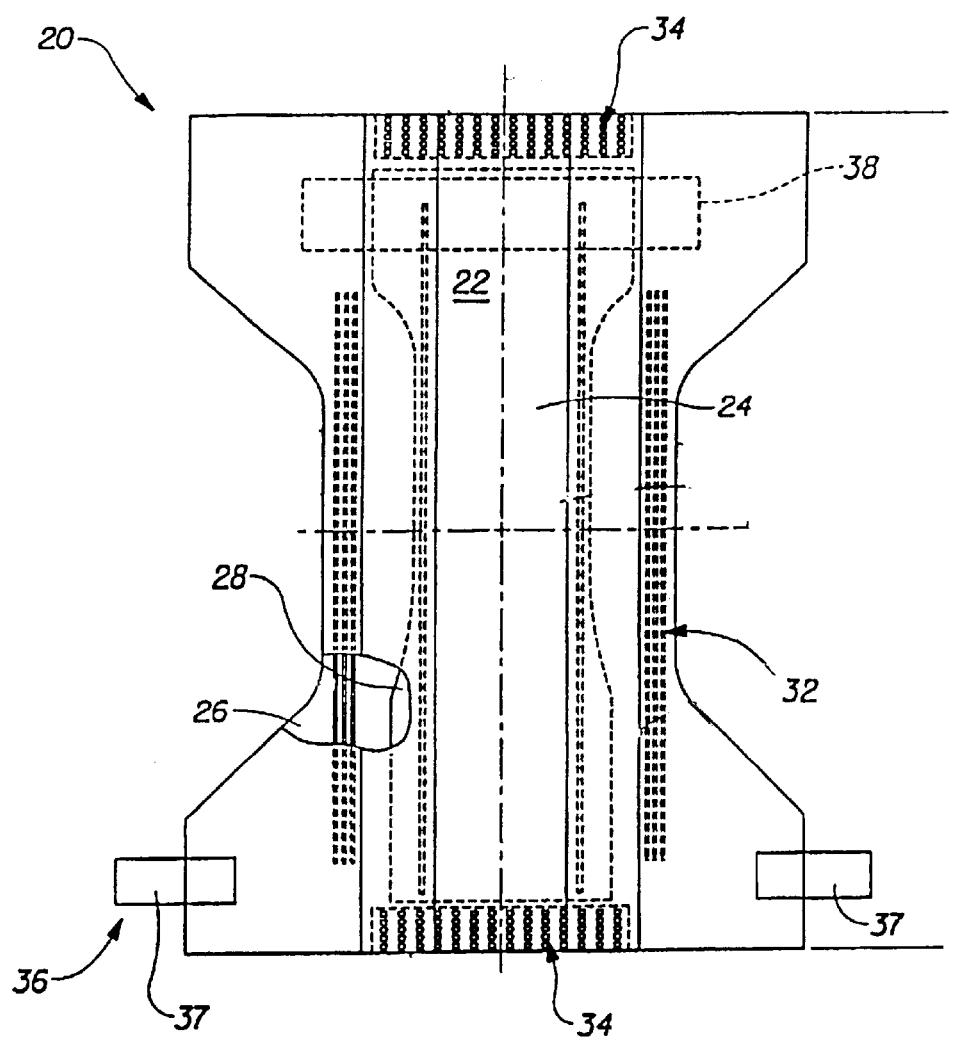

THERMOCALENDERED NON-WOVEN ELASTIC LAMINATE

CROSS-REFERENCE TO RELATED APPLICATION

This is a continuation-in-part of application Ser. No. 09/370,344, filed Aug. 6, 1999 now abandoned.

BACKGROUND OF THE INVENTION

The present invention relates generally to laminate elastic fabrics, and more particularly to elastic fabrics that are comprised of a non-woven layer laminated to an elastic layer, the laminate being formed by a controlled combination of temperature and pressure to render the laminate with a specific elastic performance.

The prior art contains a number of examples of laminate elastic fabrics comprised of a non-woven layer and an elastic layer. Such fabrics are useful for applications such as garments, disposable medical products, personal hygiene products, industrial products, and diapers. Depending on the particular application, the fabric may require particular properties such as a desired degree of elongation/recovery, porosity, softness, etc. These properties may be influenced by the selection of the particular non-woven component layer and the elastic component layer.

To construct the non-woven laminate elastic, the non-woven layer may be laminated to the elastic component layer with a chemical bond, mechanical bond, or by thermal bonding. Tension may be applied to either the elastic member or the non-elastic member prior to laminating to provide the final fabric with its elastic elongation capability. In these various methods of fabrication, the recovery capability of the laminate is a function only of the recovery of the elastic member.

When the elastic layer is stretched prior to joining the layers, the non-woven layer then "gathers" between the bond points when the laminate is relaxed, with the laminate surface disadvantageously showing "puckering". Also, this method of fabricating an elastic laminate results in only a limited elongation potential, as an effect called "positive stop" limits laminate extension to the physical limits of the non-woven gathered between the bonded points. Such a process is disclosed in U.S. Pat. No. 4,720,415, and U.S. Pat. No. 4,842,596, incorporated herein by reference.

Alternatively, the non-woven layer can be tensioned prior to joining a tensioned or relaxed elastic member. When relaxed, the laminate fabric again shows a puckered surface with "gathers" of the non-woven between bond points. The previously described "positive stop" feature is also again manifested by the extension of the gathers in the non-woven layer when tension is applied. Also, this method produces a dimensional distortion in the non-woven layer referred to as "necking" or "necking in". Several variations of this process are disclosed in U.S. Pat. Nos. 4,981,747; 5,226,992; 5,336,545; and 5,514,470; incorporated herein by reference.

These methods produce laminates that exhibit stretch and recovery primarily oriented in the direction of the applied tension, the machine direction ("MD"). Little or no stretch and recovery is induced in the cross tension direction ("CD"). Achieving a degree of elastic stretch and recovery in the CD has been significantly more difficult than the MD.

U.S. Pat. No. 5,114,781, incorporated herein by reference, discloses a method for producing a laminate, which has CD elastic stretch and recovery. The process disclosed is based on laminating a 'reversibly necked' substrate under tension to a tensioned elastic member. The provided definition of a 'reversibly necked' fabric is one that has been treated in some way while in a tensioned, necked-in state to impart memory to the material. The effect of this memory is to induce the fabric to return to its necked-in configuration after tension is applied in the CD. The fabric and method disclosed, however, result in a fabric surface that is puckered and gathered as the necked-in fabric is bonded to a tensioned elastic layer. Also, the reversible necking of the non-elastic layer requires an additional process step with associated costs and efforts.

Thus it is made apparent that the tensioning processes generally disclosed in the prior art have associated shortcomings. The practice has resulted in fabrics generally having only MD elasticity, at the expense of elasticity in the CD. Among other factors, this has resulted from the requirement of tensioning either the elastic or non-elastic layers or both when the layers are bonded together. While significant tensioning may be achieved in the MD, it is much more difficult to achieve in the CD, particularly simultaneously with the MD tensioning as MD tensioning in the MD may cause the CD dimension to be reduced or "necked in", and to thereby lose CD elongation capacity.

Further, tensioning results in fabrics having a disadvantageously gathered or puckered surface, and limited elongation. Equipment and process controls are required for tensioning that are far more complex, expensive, and difficult to maintain than a standard lamination processing line. Finally, the fabrics of the prior art have offered only limited elastic recovery, particularly after multiple elongation cycles.

A heretofore unresolved need therefore exists for an improved process for making an elastic laminate non-woven fabric, and likewise for an improved elastic laminate non-woven fabric.

OBJECTS OF THE INVENTION

It is an object of the invention to provide a process for making a non-woven elastic laminate fabric having a high degree of CD elongation.

It is a further object of the invention to provide a process for making a non-woven elastic laminate fabric having a high degree of elastic recovery, the laminate being formed by a controlled combination of temperature and pressure to render the laminate with a specific elastic performance.

It is a further object of the invention to provide a non-woven elastic laminate fabric having a high degree of CD elongation.

It is a still further object of the invention to provide a non-woven elastic laminate fabric having a high degree of elastic recovery, the laminate being formed by a controlled combination of temperature and pressure to render the laminate with a specific elastic performance.

SUMMARY OF THE INVENTION

The present invention comprises a method for making a non-woven elastic laminate fabric, as well as the elastic laminate fabric produced thereby, the laminate being formed by a controlled combination of temperature and pressure to render the laminate with a specific elastic performance.

The elastic non-woven laminate fabric of the invention comprises a non-woven fabric web having a CD elongation of at least 120% and a basis weight of between about 10–100 gm/m² laminated to an elastic film layer comprised of a vinylidene isoprene polymer having a thickness of between 0.5 to 3.5 mils. The resulting elastic laminate non-woven fabric of the invention has CD elongation of at least 120%, MD elongation of 25–70%, and a CD elastic recovery of at least 85% after multiple cycles of 100% elongation.

It is noted that % elongation as used herein may be defined as:

$$\text{elongation \%} = 100 \times \left[\left(\frac{\text{elongation length} - \text{original length}}{\text{original length}}\right)\right]$$

Thus if a fabric is 10 in. long in a relaxed original state, and may be stretched to 25 in, then it shows 150% elongation. Further, as used herein % recovery may be defined as:

$$\text{recovery \%} = 100 \times \left[\left(\frac{\text{elongated length} - \text{final/relaxed length}}{\text{elongated length} - \text{original length}}\right)\right]$$

Thus if the above fabric returned to a relaxed final state of 15 in., then it shows 67% recovery.

Preferably, the non-woven web component of the fabric of the invention has a CD elongation of at least 150% and a basis weight of between about 15–50 gm/m². The preferred non-woven web may comprise spunbond or meltblown filament webs, or hydroentangled, carded staple fibers. Preferred materials of composition for the non-woven web of the invention include poly(ethylene terephthalate) ("PET") and polyolefins.

The use of the preferred film also provides advantages over the use of elastic net-like structures or reticulated films in that more uniform elongation and a more uniform, wrinkle free surface appearance result. The film is preferably extrusion coated onto the non-woven web, while the web is in a relaxed, un-tensioned state (except for tensioning as may be required for normal web processing). The preferred extrusion coating of the film onto the non-woven web results in a final fabric having a smooth, ungathered or puckered surface, as all components are joined in an effectively relaxed configuration. Further, extrusion coating provides for large bonding interface area between layers, so that a coherent final laminate fabric results. Other means of attachment comprise bonding with an adhesive or thermal bonding by calendering.

The fabric of the invention has a CD elongation of at least 120% and preferably greater than 150% that is superior to that of elastic non-woven laminates of the prior art. Further, the elastic recovery of the fabric of the invention, which is 85% or greater after several cycles of 100% elongation, is also superior to that of any prior art elastic non-woven laminate fabric.

A preferred embodiment of the laminate elastic fabric of the invention comprises an elastic layer sandwiched in between two non-woven outer layers. A first non-woven web is as described above, with a CD elongation of at least 120%, with at least 150% most preferred, and a basis weight of between about 10–50 gm/m². An elastic vinylidene isoprene film, with a thickness of between about 0.5–3.5 mils, is laminated onto the web. Finally, a second non-woven web having a CD elongation of at least 120% as well as other physical properties and characteristics that may be substantially similar to the first web, including basis weight, is thermally bonded to the exposed side of the film with the film thereby sandwiched between the two non-woven layers. The temperature and pressure used to perform the lamination having a pronounced effect on physical performance.

The method of the invention generally comprises the steps of providing a non-woven fabric web having a CD elongation of at least 120% and a basis weight of between 10–50 gm/m², attaching an elastic film to the non-woven web with both the web and the film in substantially relaxed, unstretched states. The film comprises a vinylidene isoprene polymer with a thickness of between about 0.5 and 3.5 mils. The preferred means of attachment of the film to the non-woven web is by extrusion coating. As both the elastic and non-woven layers are in substantially relaxed, unstretched states when joined, the final laminate fabric of the invention has a smooth surface free from the puckering and/or gathering of non-woven elastic laminates of the prior art.

The preferred non-woven web provided in the method of the invention is as generally described above in relation to the preferred fabric of the invention. It has a CD elongation of at least 150% and a basis weight of between about 10–100 gm/m². The web may comprise spunbond or meltblown continuous filaments, or more preferably hydroentangled, or highly randomized, carded staple fiber webs. The web may be prepared in line with the joining of the layers, or may be prepared separately. Preferred materials of composition include polyolefins, and polyesters (PET), polyamides, and the blends thereof.

The preferred vinylidene isoprene polymer film of the method of the invention is also as described above in association with the preferred fabric of the invention. Most preferably the film has a thickness in range of about 2.0 to 2.5 mils.

A preferred embodiment of the method of the invention comprises the steps of providing a first non-woven web having a CD elongation of at least 120%, with at least 150% most preferred, and a basis weight of between about 10–50 gm/m². Next, an elastic vinylidene isoprene film is extrusion coated onto the web in a thickness as described above, including preferred ranges. A second non-woven web having physical properties and characteristics similar to the first web, including basis weight and CD elongation, is then thermally bonded to the exposed side of the film with both the second web and the first web and film laminate in substantially relaxed, unstretched states. The film is thereby sandwiched between the two non-woven layers.

The thermal point bonding of the second layer to the exposed side of the film can be carried out at a temperature in the range of the melting temperature of the film, to result in an intimate co-mingled bond between both outer non-woven layers and the film layer therebetween.

It has been found that subtle variations in the bonding temperature and pressure during the lamination process yield constructs of differing performance. Two particularly preferred sets of bonding temperatures and pressures are referred to those yielding a "high-bond" and a "low-bond". Both high-bond and low-bond materials are formed by the application of an engraved calender roll having a discontinuous bond pattern with no greater than about 15% land area. The high bond materials incorporate the use of the engraved calender roll at a temperature in the range of about 360° F. to 390° F. The low-bond materials incorporate the use of the engraved calender roll at a temperature in the range of about 340° F. to 360° F. The pressure of the engraved calender roll for the manufacture of the high-bond material versus the low-bond is increased by no more than about 10%.

An optional, additional step in the method of the invention further comprises tensioning the laminated fabric of the invention in the machine direction after joining of the layers in a calender nip and before winding the fabric onto a winder. The tension is released before winding, so that the fabric is wound in a relaxed state. The tensioning causes some bonds to break in the nonwoven fabric layers. This breakage increases the overall elongation capacity of the laminate fabric, and decreases the stretch force of the laminate fabric.

The method of the invention thereby provides an improved process for making an elastic non-woven laminate fabric that does not require applying unusual tension to or otherwise stretching either the non-woven layer(s) or the elastic layer, instead allowing fabrication while the layers are in a substantially relaxed, un-extended state. The present invention therefore avoids the additional efforts and expenses associated with the stretching of one or all of the layers during processing, specifically the specialized equipment and process controls required to provide and maintain a tensioning station in the production line.

Further, the method of the invention is a simpler and more efficient method than those of the prior art. Also, the method of the invention results in a fabric having CD elongation of at least 120%, and elastic recovery of at least 85% after 3 cycles of 100% elongation.

The above brief description sets forth rather broadly the more important features of the present disclosure so that the detailed description and examples that follow may be better understood, and so that the present contributions to the art may be better appreciated. There are, of course, additional features of the disclosure that will be described hereinafter which will form the subject matter of the claims appended hereto. In this respect, before explaining the several embodiments of the disclosure in detail, it is to be understood that the disclosure is not limited in its application to the details of the construction and the arrangements set forth in the following description or illustrated in the drawings. The present invention is capable of other embodiments and of being practiced and carried out in various ways, as will be appreciated by those skilled in the art. Also, it is to be understood that the phraseology and terminology employed herein are for description and not limitation.

BRIEF DESCRIPTION OF THE FIGURES

FIG. 1 shows a schematic diagram of the preferred method of the invention;

FIG. 2 shows a cross section view of the preferred fabric of the invention; and

FIG. 3 is a plan view of a disposable absorbent article, illustrated as a disposable diaper, embodying the present invention.

DETAILED DESCRIPTION AND EXAMPLES

Turning now to FIG. 1, a schematic of the preferred method of making a laminated non-woven elastic fabric is shown. A first non-woven layer 2 having a CD elongation of at least 120%, and more preferably 150%, is unwound from roller 4. Non-woven 2 has a MD elongation in the range of 25–70%, with 25–45% most common. In general, the lower the MD/CD elongation ratio, the higher the CD elongation; i.e. the more CD orientation of the fibers/filaments, the greater the CD elongation. Non-woven layer 2 may comprise spunbond or meltblown filament webs, or hydroentangled or carded staple fibers webs, such as highly randomized carded staple fiber webs. Hydroentangled webs and highly randomized, carded webs that are adhesive or thermal bonded are preferred.

Preferred materials of composition for web 2 are polyolefins and PET. A preferred basis weight for web 2 is between about 10–100 gm/m$^2$, with 15–50 gm/m$^2$ most preferred. Table 1 lists some examples of suitable non-woven substrates layers and associated CD tensile characteristics that may be used in the method and fabric of the invention (the non-woven substrates of the invention are not limited to the examples of Table 1).

Elastic film 6 comprised of a vinylidene isoprene polymer having a thickness of between 0.5 to 3.5 mils is extrusion coated onto non-woven web 4 by extruder 8, while both film 6 and web 2 are in substantially relaxed, unstretched states, except that web 2 is under normal tension as may be required to unwind and to otherwise process it.

The preferred vinylidene isoprene polymer film 6 of the fabric of the invention has a thickness of about 2 mils, and comprises 70–95% of a block copolymer with the general formula $A-B-R-(B-A)_n$ where A is a monovinylidene aromatic monomer, B is a conjugated diene, R is a remnant of a multifunctional coupling agent, and n is an integer from 1–5. A second preferred film composition comprises 70–95% of a block copolymer with the general formula $A_x-(BA)_y-BA$ where A is a monovinylidene aromatic monomer, B is a conjugated diene, x is from 0–1, and y is from 0–3. A commercial version of the preferred film is available under the VECTOR tradename from the Dexco Corp., a Dow Chemical, Exxon Chemical joint venture in Plaquemine, La.

Second non-woven layer 10 is next unwound from roller 12 and deposited on the exposed side of film 6. Non-woven web 10 is deposited in a substantially relaxed, unstretched state to a likewise un-tensioned web 2/film 6 laminate. That is, the three layers are not tensioned, stretched, necked, elongated, or otherwise subjected to additional tensioning at the time they are joined together beyond that required by the process to maintain alignment of the fabrics through the process (this is the general meaning intended to be applied throughout this application to the general description of "being substantially relaxed and un-tensioned"). The resultant fabric of the invention thereby advantageously has a surface that is not wrinkled, bunched, or gathered.

The novel method of attachment of the elastic film to the non-woven layer of the invention with both layers in substantially un-tensioned, relaxed states further provides the fabric of the invention with greater CD elongation and recovery capacities than fabrics of the prior art. The principal methods of the prior art rely on applying excessive tension in the MD during the consolidation of the laminates. When it is the elastic member that is tensioned in this manner, very little CD elongation capacity remains, and the structure is locked in this configuration during the bonding step. When it is the non-woven layers that are "necked in" or tensioned, only limited CD elongation results contributed entirely by the amount of fabric in the gathers and limited to those gathered fabric dimensions when the gathers are pulled out.

Non-woven layer 10 may have substantially the same physical characteristics as first non-woven layer 2, and likewise may be comprised of the same materials. On the other hand, non-woven layer 10 may have different physical properties from first non-woven layer 2, or be comprised of different materials, as may be desired. It is critical, however, that the second non-woven layer 10 has a CD elongation of at least 120%, and preferably of at least 150%. Table 1 above is referred to for examples of suitable webs for comprising non-woven layer 10.

Heated, engraved, calender rolls 14 thermally bond second non-woven layer 10, film 6, and first non-woven layer 2. Thus film 6 is sandwiched between outer non-woven web layers 2 and 10. Preferably, calender rollers 14 operate at a temperature in the melting range of film 6 so that an integral bond results between all three layers, with fibers or filaments in the outer nonwoven layers thereby intermingled with the film layer at the bond point. Film 6 is actually observed to thin at the bond points.

In the preferred embodiment of the method of the invention as depicted in FIG. 1, after calendering with calender rollers 14, the laminated fabric 16 of the invention is tensioned in the MD with tension rollers 18. Tensioning in the MD breaks some of the fibers in the outer non-woven layers, leading to increased MD elongation and decreased stretch force in fabric 16, as well as generally improved hand. Tension in fabric 16 is released after passing tension rollers 18, and laminated elastic fabric 16 is finally wound on roller 20 in a substantially relaxed, un-stretched state.

FIG. 2 is a cross section of a preferred fabric 16 of the invention, as produced by the preferred process described above. Fabric 16 comprises outer non-woven layers 2 and 10 sandwiching elastic film layer 6. Non-woven outer layers 2 and 10 must have a CD elongation of at least 120%, and preferably of at least 150%. They preferably have a basis weight in the range of 15–50 gm/m$^2$, and may comprise spunbond or meltblown continuous filaments, or hydroentangled, carded, highly randomized staple fibers. Preferred materials of composition comprise polyolefins, polyesters, polyamides, and the combinations thereof Reference is made to Table 1 above for examples of suitable non-woven layers. As illustrated in FIG. 2, the preferred fabric of the invention has a surface that is substantially flat and is not bunched, gathered, or necked in. This results from the outer nonwoven web layers 2 and 10 being in substantially unstretched, relaxed states when attached to film layer 6.

Preferred elastic film 6 is the VECTOR film as described above, available from the Dexco Corp., in Plaquiemine, La.; with a preferred thickness of between about 0.5 and 3.5 mils, with a most preferred thickness in the range of about 2.0 to 2.5 mils. Preferably, film 6 is extrusion coated onto first non-woven layer 2, with non-woven layers 2 and 10 and film layer 6 then thermally point bonded together at a temperature in the melting range of film 6 to achieve an integral bond between all three layers.

The preferred laminate fabric of the invention has a CD elasticity of at least 120% and most preferably greater than 150% that is superior to that of elastic non-woven laminates of the prior art. Further, the CD elastic recovery of the fabric of the invention, which is 85% or greater after several cycles of 100% elongation, is also superior to that of prior art elastic non-woven laminate fabrics. It is noted that the nature of the non-woven layers significantly affects the recovery of the laminate fabric. Non-woven fabrics show hysteresis recovery when cycled to limits below their yield point. The higher the overall elongation of the non-woven, the more recovery power the fabric will be able to contribute to the laminate recovery. So, a laminate made with a non-woven substrate having 120% elongation would be expected to provide a lower elastic recovery from a 100% extension than a laminate prepared with a substrate having 175% elongation.

A comparison between several elastic laminate fabrics of the invention and prior art elastic laminate fabrics is provided in Table 2. The "Comparative Examples" in Table 2 are elastic laminate fabrics that are commercially available, where "SB" is spunbond, "PP" is polypropylene, and "PE" is polyethylene. "Elastic Film" of Table 2 is an extruded film of the described VECTOR film polymer. The "Elastic Laminates" of Table 2 identify several fabrics of the invention prepared according to the method of the invention, where "HEF" indicates hydroentangled fabric, and "PET" is poly (ethylene terephthalate). The "Tensioned Fabrics" of Table 2 indicate fabrics that have been tensioned as described above (at 18 in FIG. 1) after lamination.

Table 2 illustrates the superior recovery of the fabrics of the invention over prior art fabrics. Table 2 also shows the reduced elastic force of the fabrics of the invention over prior art fabrics. Thus the fabrics of the invention combine increased recovery with reduced elastic force over prior art fabrics, which is a surprising result of the fabric and method of the invention as typically increased recovery is only achieved through increased elastic force. The fabrics of the invention are able to achieve a relatively gentle retractive force through their unique method of fabrication; and particularly due to the use of the vinylidene isoprene film of the invention.

The high level of recovery after multiple extensions that the fabrics of the invention show is a result of their unique design. Because the laminated layers are joined without application of tension, there is no initial introduction of stress during formation to structurally deform the non-elastic members or to reduce the elasticity of the elastic member. As the non-elastic member is not under excessive tension during manufacture of the laminate, the natural recovery of the high elongation fabric is able to contribute to the recovery performance of the final laminate fabric.

Table 3 illustrates the advantageous effects subtle variations in temperature and pressure have on the performance of the laminate construct manufactured in accordance with the present invention. Initial constructs were formed from the combination of two outer layers of extensible 26.5 gram per square meter HEF PET fabric and an elastic inner vinylidene isoprene film layer at a thickness about 3.5 mil. The constructs where then individually laminated at the low-bond and high-bond conditions as indicated. As can be seen from the physical property testing, stretch and recovery performance and tear strength can be tuned utilizing alteration of bond temperature and pressure.

A number of end-use articles can be benefit from the inclusion or substitution of an elastic material layer with the elastic laminate of the present invention, including, but not limited to, hygiene absorbent articles, such as diapers and catamenial products, and medical/industrial protective articles.

Disposable waste-containment garments, are generally described in U.S. Pat. No. 4,573,986, U.S. Pat. No. 5,843,056, and U.S. Pat. No. 6,198,018, which are incorporated herein by reference.

An absorbent article incorporating a vinylidene/ nonwoven elastic laminate of the present invention is represented by the unitary disposable absorbent article, diaper 20, shown in FIG. 3. As used herein, the term "diaper" refers to an absorbent article generally worn by infants and incontinent persons that is worn about the lower torso of the wearer. It should be understood, however, that the present invention is also applicable to other absorbent articles such as incontinence briefs, incontinence undergarments, diaper holders and liners, feminine hygiene garments, training pants, pull-on garments, and the like.

FIG. 3 is a plan view of a diaper 20 in an uncontracted state (i.e., with elastic induced contraction pulled out) with portions of the structure being cut-away to more clearly show the construction of the diaper 20. As shown in FIG. 3, the diaper 20 preferably comprises a containment assembly 22 comprising a liquid pervious topsheet 24; a liquid impervious backsheet 26 joined to the topsheet; and an absorbent core 28 positioned between the topsheet 24 and the backsheet 26. The absorbent core 28 has a pair of opposing longitudinal edges, an inner surface and an outer surface. The diaper can further comprise elastic leg features 32; elastic waist features 34; and a fastening system 36 which preferably comprises a pair of securement members 37 and a landing member 38.

Practical application of an elastic laminate, and preferably a strong, highly elongateable fabric, as the primary constituent in the elastic leg features 32, elastic waist feature 34, and securement member 37 results in a diaper that is more flexible and therefore more conforming to deformation of the overall structure as the diaper is worn. Further, as the backsheet is subjected to frictional contact with the user's environment, the absence of pleats, corrugations, or other surface variances aid in ensuring that the overall diaper construct does not fail structurally while the diaper is in use.

Medical and industrial protective products, such as medical gown, surgical drape and oversuits can benefit significantly from the inclusion of the elastic laminate of the present invention. Of particular utility in the fabrication of such protective products is the application of the elastic laminate in cuff areas, neck regions, and fitments whereby the recoverable elongation and strength attribute improves product performance and wearer comfort. Patents generally describing such protective products include U.S. Pat. Nos. 4,845,779, 4,876,746, 5,655,374, 6,029,274, and 6,103,647, which are incorporated herein by reference.

TABLE 1

| Sample | Fabric Basis Wt. (gm/m²) | CD Tensile (gm) | CD Elongation (%) |
|---|---|---|---|
| Carded PP staple fiber | 40 | 645 | 151 |
| Hydroentangled PET staple fiber | 24 | 128 | 222 |
| Apertured hydroentangled PET staple fiber | 31 | 710 | 152 |
| Hydroentangled PET staple fiber | 57 | 1,772 | 104 |

TABLE 2

| Fabric | Fabric Basis Weight (gm/m²) | Elastic Force (gm) @ 100% CD Elongation | | | % Elastic Recovery after 3rd 100% CD Cycle |
|---|---|---|---|---|---|
| | | Cycle 1 | Cycle 2 | Cycle 3 | |
| Comparative Examples (prior art) | | | | | |
| SB-PP | 138 | 1,021 | 998 | 828 | 75 |
| SB-PE with Film | 105 | 705 | 658 | 637 | 81 |
| SB-PP with Film | 98 | 1,615 | 1,388 | 1,306 | 80 |
| Film alone | 59 | 272 | 249 | 249 | 94 |
| Elastic Laminates of the Invention | | | | | |
| HEF-PET with Film | 111 | 892 | 650 | 544 | 88 |
| HEF-PET with Film | 117 | 514 | 431 | 393 | 91 |
| Carded PP with Film | 140 | 665 | 575 | 529 | 89 |
| Tensioned Fabrics of the Invention | | | | | |
| Carded PP with Film | 145 | 416 | 386 | 363 | 89 |
| Carded PP with Film | 165 | 302 | 272 | 265 | 90 |

TABLE 3

| Material | Basis Weight | Bond Temp (° F.) | Bond Pressure (psi) | Elastic Force (gm) @ 100% CD Elongation | | | % Elastic Recovery after 3rd CD Cycle | Tear Strength (g/in) |
|---|---|---|---|---|---|---|---|---|
| | | | | Cycle 1 | Cycle 2 | Cycle 3 | | |
| 3.5 mil High Bond | 144 | 30– | 65 | 740 | 600 | 534 | 88 | 2800 |
| 3.5 mil Low Bond | 145 | 360 | 60 | 322 | 289 | 266 | 92 | 897 |

The advantages of the disclosed invention are thus attained in an economical, practical, and facile manner. While preferred embodiments and example configurations have been shown and described, it is to be understood that various further modifications and additional configurations will be apparent to those skilled in the art. It is intended that the specific embodiments and configurations herein disclosed are illustrative of the preferred and best modes for practicing the invention, and should not be interpreted as limitations on the scope of the invention as defined by the appended claims.

What is claimed is:
1. An elastic non-woven laminate fabric, comprising:
 a) a first and second non-woven fabric web comprised of thermoplastic polymers, said web having a CD elongation of at least 120% and a basis weight of between about 10–100 gm/m²;
 b) an elastic film comprised of a vinylidene isoprene polymer; said film having a thickness of between about 0.5 to 3.5 mils; said elastic film attached to said first and second non-woven webs with said film and said web in substantially relaxed, un-elongated states; and the elastic non-woven laminate fabric having a CD elongation of at least 120% with an elastic recovery of at least 85% after three cycles of 100% elongation;

c) said elastic film being juxtaposed between said first and second nonwoven web in a laminate construction; and d) said laminate construction having a discontinuous bond pattern of no greater than 15% land area.

2. An elastic non-woven laminate fabric as in claim 1, wherein said non-woven fabric has an elastic CD recovery of at least 90% after three cycles of 100% elongation.

3. An elastic non-woven laminate fabric as in claim 1; wherein said non-woven web and the elastic laminate fabric each have CD elongation of at least 150%.

4. An elastic non-woven laminate fabric as in claim 1; wherein said elastic film is extrusion coated on said non-woven web.

5. An elastic non-woven laminate fabric as in claim 1, wherein said non-woven web comprises a member chosen from the group consisting of spunbond continuous filaments, meltblown continuous filaments, hydroentangled carded staple fibers, thermally bonded carded staple fibers, and adhesively bonded carded staple fibers.

6. An elastic non-woven laminate fabric as in claim 1; further comprising a second non-woven web attached to said film.

7. An elastic non-woven laminate as in claim 6, wherein said second non-woven web is attached to said film by thermal calendering at a temperature in the melting range of said film.

8. An elastic non-woven laminate fabric as in claim 1; wherein said vinylidene isoprene film has a thickness in the range of about 2.0 to 2.5 mils.

9. An elastic non-woven laminate fabric as in claim 1; wherein said vinylidene isoprene film comprises 70–95% of a block copolymer with a general formula chosen from the group consisting of:

$A_x$–$(BA)_y$–BA where A is a monovinylidene aromatic monomer, B is a conjugated diene, x is from 0–1, and y is from 0–3; and A-B-R-$(B-A)_n$ where A is a monovinylidene aromatic monomer, B is a conjugated diene, R is a remnant of a multifunctional coupling agent, and n is an integer from 1–5.

10. An elastic non-woven laminate fabric as in claim 1; wherein said non-woven web has a basis weight of about 15–50 gm/m$^2$.

11. An elastic non-woven laminate fabric as in claim 1; wherein said laminate fabric further comprises a substantially smooth surface free of puckers or gathers.

12. An elastic nonwoven laminate fabric as in claim 1; wherein said laminate fabric is used in the construction of protective apparel.

13. A disposable waste-containment garment, comprising;

an absorbent core, a liquid pervious topsheet, a liquid impervious backsheet, a number of elastic fitments, one or more of said elastic fitments comprising an elastic laminate, said elastic laminate comprising:
  i) a first and second non-woven fabric web comprised of thermoplastic polymers, said web having a CD elongation of at least 120% and a basis weight of between about 10–100 gm/m$^2$;
  ii) an elastic film comprised of a vinylidene isoprene polymer; said film having a thickness of between about 0.5 to 3.5 mils; said elastic film attached to said first and second non-woven webs with said film and said web in substantially relaxed, un-elongated states; and the elastic non-woven laminate fabric having a CD elongation of at least 120% with an elastic recovery of at least 85% after three cycles of 100% elongation;
  iii) said elastic film being juxtaposed between said first and second nonwoven web in a laminate construction; and
  iv) said laminate construction having a discontinuous bond pattern of no greater than 15% land area.

14. A disposable waste-containment garment as in claim 13, wherein the garment is a diaper.

* * * * *